(12) United States Patent
Lavi et al.

(10) Patent No.: US 11,684,399 B2
(45) Date of Patent: Jun. 27, 2023

(54) HALF PINS FOR EXTERNAL FIXATORS

(71) Applicant: Orthex, LLC, Warsaw, IN (US)

(72) Inventors: Abraham Lavi, Delray Beach, FL (US); Dror Paley, West Palm Beach, FL (US); Victor Lavi, Delray Beach, FL (US)

(73) Assignee: Orthex, LLC, Warsaw, IN (US)

( * ) Notice: Subject to any disclaimer, the term of this patent is extended or adjusted under 35 U.S.C. 154(b) by 0 days.

(21) Appl. No.: 17/655,796

(22) Filed: Mar. 22, 2022

(65) Prior Publication Data

US 2022/0211420 A1   Jul. 7, 2022

Related U.S. Application Data

(63) Continuation of application No. 16/444,612, filed on Jun. 18, 2019, now Pat. No. 11,291,486.

(60) Provisional application No. 62/686,891, filed on Jun. 19, 2018.

(51) Int. Cl.
| | |
|---|---|
| *A61B 17/84* | (2006.01) |
| *A61B 17/62* | (2006.01) |
| *A61B 17/64* | (2006.01) |
| *A61B 17/88* | (2006.01) |
| *A61B 17/00* | (2006.01) |

(52) U.S. Cl.
CPC ............ *A61B 17/846* (2013.01); *A61B 17/62* (2013.01); *A61B 17/6416* (2013.01); *A61B 17/8875* (2013.01); *A61B 2017/00889* (2013.01)

(58) Field of Classification Search
CPC ...... A61B 17/846; A61B 17/86; A61B 17/863
See application file for complete search history.

(56) References Cited

U.S. PATENT DOCUMENTS

| | | | | |
|---|---|---|---|---|
| 5,180,382 A | * | 1/1993 | Frigg | A61B 17/863 606/65 |
| 5,259,398 A | * | 11/1993 | Vrespa | A61C 8/0025 411/413 |
| 2007/0233124 A1 | * | 10/2007 | Corrao | A61B 17/863 606/327 |

\* cited by examiner

*Primary Examiner* — Kevin T Truong
*Assistant Examiner* — Tracy L Kamikawa
(74) *Attorney, Agent, or Firm* — John V. Daniluck; Gerald W. Roberts; Dentons Bingham Greenebaum LLP

(57) ABSTRACT

The invention is a half pin for use in conjunction with external fixators, in which the half pin has a thin hydroxyapatite coating over a substantial portion thereof, a not-sharp hole-finding tip, and a variable pitch pattern in the threaded portion of the half pin. The hydroxyapatite coating must be thin—40-70 microns, deposited by plasma spray—and with limited porosity and pore size, and must extend not only over all the threads of the half pin but also a substantial portion of the unthreaded shaft proximal to the threaded end. The invention also includes a pin cube for use in association with the coated half pins. Wires may also be coated with the hydroxyapatite coating.

8 Claims, 7 Drawing Sheets

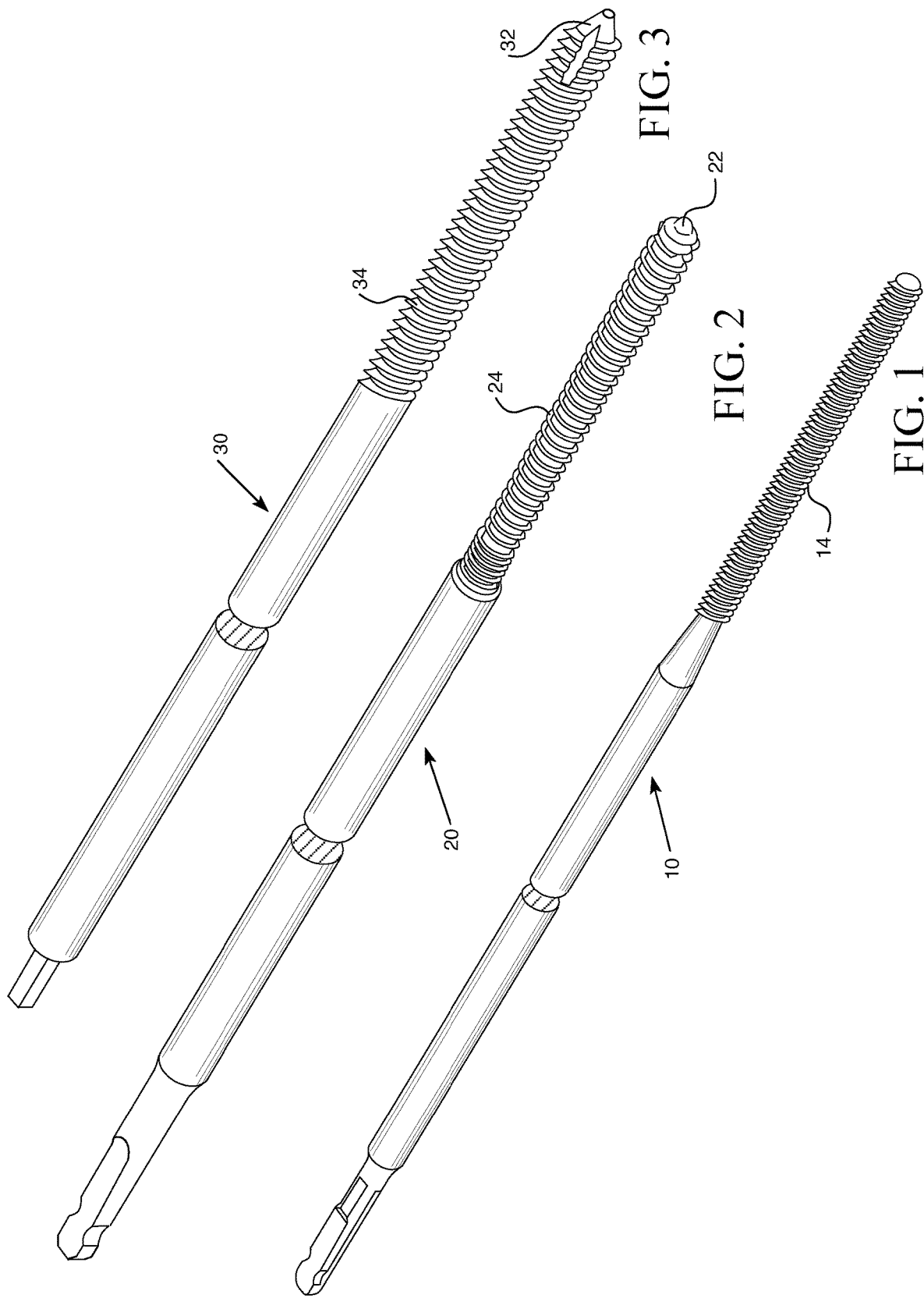

HALF PINS FOR EXTERNAL FIXATORS

CROSS REFERENCE TO RELATED APPLICATIONS

This application is a continuation of U.S. patent application Ser. No. 16/444,612, filed Jun. 18, 2019, which claims the benefit of priority to U.S. Provisional Patent Application Ser. No. 62/686,891, filed Jun. 19, 2018, both of which are incorporated herein by reference.

FIELD OF THE INVENTION

The present invention relates to improvements in orthopedics and restorative musculoskeletal procedures of various types and extents. More particularly, the invention pertains to half pins, that is, the connecting structures between external fixator hardware and the bone or bones for which such external fixators are intended, as well as a pin cube well suited to anchor such half pins.

BACKGROUND OF THE INVENTION

Many individuals alive today remember a time well before external fixators became widely used, and thus recall the wonder and consternation—predictable, if not inevitable—upon viewing "a halo" or, indeed, any external bone fixator for the first time. Patients in need of bone repair and stabilization learned almost immediately, moreover, that after the installation of their external fixator hardware, cleanliness and hygiene issues would almost certainly require focused patient self-care, such as cleansing each insertion point one or more times a day with, say, a swab and isopropanol or other antiseptic solution. For those unaccustomed to dealing with unbandaged breaches in the skin and adjacent tissue, many found this process to be unnerving. Any "Yuck factor" aside, from the earliest days of external fixator technology a heretofore-unmet need has persisted for the best possible management—and enhancement—of skin and adjacent tissue hygiene control and protection. At the same time, improvements in the fixator technology itself have been needed to address issues, including but not limited to, accuracy of bone fixation, angles for optimized anchoring for both bones and hardware, improved durability of hardware while at the same time reducing bulk and weight, and so forth.

Paramount in the physicians' minds, too, if not the patients', are the "safe corridors" in which external fixators may be anchored. As explained for example in Nayagam, Selvadurai, "Safe Corridors in External Fixation: the Lower Leg (Tibia, Fibula, Hindfoot and Forefoot)," *Strategies Trauma Limb Reconstr.*, Vol. 2, No. 2, pp. 105-110 (December 2007), physicians must know where it is safe to position the anchoring wires or half pins of an external fixator and, fortunately, as a matter of anatomy, there are indeed clear spaces through which fixator wires or half pins may traverse the patient tissue. Because neurovascular structures "follow known paths around the major long bones and changes in position occur at fairly consistent levels, e.g., the common peroneal nerve winds around from posterior to anterior at the level of the neck of the fibula" [ibid.], it is typically possible to anchor external fixators by breaching predominantly only skin, muscle and any extant adipose layer or layers without affecting major circulatory, lymphatic or neurologic systems. This means, in turn, that the compatibility of the wires or half pins of an external fixator are best designed with skin, muscle and fascia in mind—and also with the ability to angulate from an external fixator only through these safe passages, which in turn requires extremely versatile hardware. A need thus remained, prior to the present invention, to determine the optimal configuration for a half pin, for use with external fixators, to maximize normal tissue preservation—while minimizing contamination and infection—while also providing optimized features for mechanics and compression to facilitate bone growth and healing. In this context, too, a need also remained for an optimized half pin design that can cooperate to give the best possible regeneration experience overall for the patient, including without limitation any or all of cleanliness, ease of insertion and removal, minimized weight and bulk, maximized load-bearing capacity, optimized lever strength, ease of securing in standard and custom external fixators and improved fastening approaches to connect the half pins (or wires) not only at their bone ends, within the patient limbs or tissue, but also at the external fixator end, with improved connectors between half pins and wires and their associated rings, hexapods, and so forth.

BRIEF DESCRIPTION OF THE FIGURES

FIG. 1 is a plan view of a first embodiment of the present half pin.

FIG. 2 is a plan view of a second embodiment of the present half pin.

FIG. 3 is a plan view of a third embodiment of the present half pin.

SUMMARY OF THE INVENTION

Figure 4:
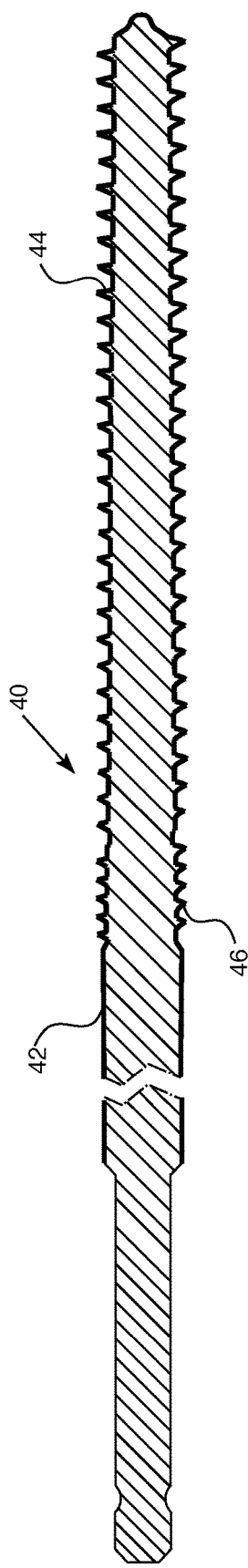
FIG. 4 is a side sectional view of the second embodiment of the present half pin as shown in FIG. 2.

In order to meet this need, the present invention is an improved half pin which, in addition to its mechanical features, is also distinctively provided with a particular hydroxyapatite coating on a specific portion—and majority surface—thereof. Importantly, the hydroxyapatite coating has a porosity of 5% or less but must indeed be porous, with a pore size no greater than 10 micrometers. Important features, then, are the porous hydroxyapatite coating, a variable thread pitch with the thread pitch's tightening along the shaft away from the half pin tip, constant major diameter threads with tapering and varying minor diameter of the threads, and an optional AO type connector at the head end of the half pin, known in the art, to connect to external fixator hardware such as rings, hexapods or rails. Ideally, the half pins are not designed to be cutting pins but are inserted in previously incised tissue and drilled channels in the bone or bones as needed, and therefore the tips of the half pins are never sharp, so a to avoid pain sensation within a patient should a half pin tip protrude from its bone into the adjacent muscle, fascia or tissue adjacent the bone. Ordinarily, the only portion of the half pin that does not contain the hydroxyapatite coating is the head end, that is, the shaft designed to interface with the external fixator hardware rings, hexapods or rails, where the hydroxyapatite would serve no biological purpose. The not-sharp, that is, truncated or rounded (nipple) hole-finding tip allows easy, manual locating of a previously cut drill hole in the intended bone site.

DETAILED DESCRIPTION OF THE INVENTION

In external bone fixation situations, the desired structures are attached to the patient's bones through threaded pins or smooth tensioned wires. The purpose of the external fixation device can be any of off-loading a particular bone, spatially manipulating one bone fragment with respect to one or more other bones, or simply preserving or distracting the soft tissue, depending on the medical indication. Prior to the present invention, it was already common to use "half pins" instead of wires, for many reasons including ease of sizing and manipulability, especially because half pins could be sized in length and diameter (and thread diameters) to match the bone size and the intended use. Prior art half pins had threads of uniform pitch, with a choice of uniform or tapered thread diameter—with the thread diameter's typically increasing from the leading end of the pin (the tip) toward the unthreaded part of the half pin. Such uniform thread pitch allowed the physician the freedom to retract the half pin when necessary without "sacrificing purchase," or without losing bone saved by the uniform pitch threads' occupying only a minimal path of affected bone. Even so, a uniform-pitch thread cannot produce compression across a fracture or osteotomy and, at best, can only partially preserve compression produced by some other means. Foremost in the minds of patients and doctors alike, too, is the need for a tissue-contacting surface on the half pin which is optimized, so that the avoidance of infection and contamination—and the insertion and removal experience from the standpoint of the patient—are as advanced and efficient as possible. Ideally, a perfect half pin forms a hygienic seal between the pin surface and the skin and muscle (and fascia and adipose, etc.) adjacent its insertion, and yet at the same time can provide a quick-release surface when the pin is to be removed, to maximize both patient comfort and avoidance of tearing, bleeding or other soft tissue damage when the external fixator is to be removed. Surprisingly, the minimally porous hydroxyapatite coating of the present invention performs both these functions.

In one embodiment of the invention, the half pin contains all of the features of: the above-described controlled-porosity hydroxyapatite coating; the variable thread pitch (tightening pitch toward the half pin head, preferably in a progression wherein a small space and chamfer connect two adjacent thread pitches rather than a gradual pitch change); constant outer (major) thread diameter, tapering inner (minor) thread diameter, and a truncated or rounded half pin tip. In this same embodiment of the invention, a titanium pin cube is used as the fastener between the half pin or pins and the external ring, hexapod or rail. An exemplary (nonlimiting) half pin of the present invention will have a variable pitch thread which decreases from a pitch distance of 2.5~2.75 mm to 1.5~1.75 mm for half pins with a thread diameter of 4.0 to 6.0 mm, and which decreases from a pitch distance of 1.5~2.5 mm to 0.75~1.5 mm for half pins having a thread diameter of 2.9~3.0 mm. The dimensions are not as important as the structures, however, which are discussed with respect to the accompanying FIGS. 1-10 in passages which follow. In other words, as long as the features as described in this specification and in the drawings are honored, the present half pins may be constructed in a wide variety of dimensions.

The hydroxyapatite coating of the present invention was counterintuitive, absent empirical trials generating data to the contrary. The inventors feared that although the hydroxyapatite would be compatible between the half pin threads and the bone in which those threads would reside, the hydroxyapatite would prove inherently incompatible with living tissue and physiological chemistry, and would be expected to create unwanted physiological effects. To our surprise, when we coated the half pins not only from the tip continuously around all the threads but then further coated the half pin shaft significantly beyond the threads (but not the whole way to the head end), in use the hydroxyapatite coating performed a remarkable antimicrobial/anti-contamination effect on the adjacent tissue AND YET the half pins were still easy to remove when desired. The ability of the hydroxyapatite to form a de facto seal for hygiene purposes, while simultaneously performing a "quick release" function where the non-threaded portion of the half pin contacted the skin and muscle areas of half pin insertion (distal to the anchoring bone) could not have been predicted, prior to the technology development of the present invention. The inventors believe that the controlled porosity of the hydroxyapatite, of under 5% with pore sizes no larger than 10 micrometers, contribute to the ability of the surrounding tissue to adhere well, but not too much, to the half pin, achieving the best-of-both of a hygiene seal and an easy pin removal dynamic. In some embodiments, the hydroxyapatite coating has between 1-5% porosity.

In order to prepare the above-described hydroxyapatite coating on a metal half pin, plasma spray technology known in the art is used to deposit a 40-70 micron coating of hydroxyapatite ceramic on the half pin, from the tip end well past the threads, covering 75-85% of the half pin length overall (as discussed below, if necessary the entire half pin may be coated). The typical metal used for half pins is surgical stainless steel or titanium alloys known in the art, although more disclosure is provided below regarding the strength and hardness features of the present half pins. The reason for the criticality of the thickness (thinness) of the hydroxyapatite coating is that outside of these tolerances and in view of the tensions that inure within the external fixators during tightening, any other coating thicknesses were subject to cracking and delamination. Presumably—by way of explanation and not to be bound thereby—hydroxyapatite coatings thinner than the present coatings did not have enough internal cohesiveness to remain intact when encountering mechanical stress, whereas thicker hydroxyapatite coatings were vulnerable to cracking and breaking as a result of their own mass and the inherent crystalline vulnerability. A key to the present invention, then, is the aforementioned thickness (and tolerances) of the hydroxyapatite coating on the half pin, specifically with its having been deposited via plasma spray, as well as the coating's presence on a substantial portion of the half pin including all of the threads and at least a portion of the non-threaded shaft nearest the head end of the half pin, taken together with the above-described porosity parameters.

In many instances, the half pins must support the patient's weight. The half pin design, in terms of outer and inner thread diameters, the cylindrical shape of the predominant shafts of the pins apart from the threads or head end connectors, and the construction of the half pins with surgical stainless steel having a Rockwell hardness of between 26-40—typically achieved by inclusion of cold worked steel in the surgical steel—all play an important part in determining mechanical strength and purchase. The present "high-duty" half pin therefore also addresses a heretofore neglected feature of bone behavior when bone is subjected to mild compressive forces. In lay terms, a mild compression applied to a live bone stimulates the bone. With external ring fixation, the patient is not allowed to put any load at all on the bone So, over time, the absence of loading may actually cause a loss in bone density—right at the time (post-surgery) that bone regeneration is wanted, not bone deterioration! The present invention therefore importantly offers a mechanism for generating mild radial stress on the bone where the present pin is inserted. In a conventional half pin, the thread pattern is uniform throughout, in terms of major diameter, minor diameter and thread pitch. In an embodiment of the present invention, however, not only is there a variable pitch transition but the pitch transition is very particularly engineered as follows: the main thread, nearest the head end of the half pin, possesses uniform pitch with a major diameter on the order of about 1.70 mm. The minor diameter (that is, the diameter of the half pin at the troughs of each thread, not the crests) increases gradually from the leading (tip) end where it is smallest, to the head end of the thread, where the minor diameter is largest. Beyond that point, the pitch decreases abruptly to about 1.2 mm just "after" a similarly abrupt (albeit subtle) reduction in the thread minor diameter, with or without an accompanying chamfer. The difference in pitch between 1.7 mm and 1.2 mm gives rise to an internal stress on the bone along the axis of the half pin, especially when the 1.2 mm pitch is matched to the cortical bone (as it will be when the half pin is fitted correctly—see below). The resultant compressive force serves as an internal bone stimulus to promote bone growth and healing right as the patient is no longer putting weight on the bone(s).

Figure 5:
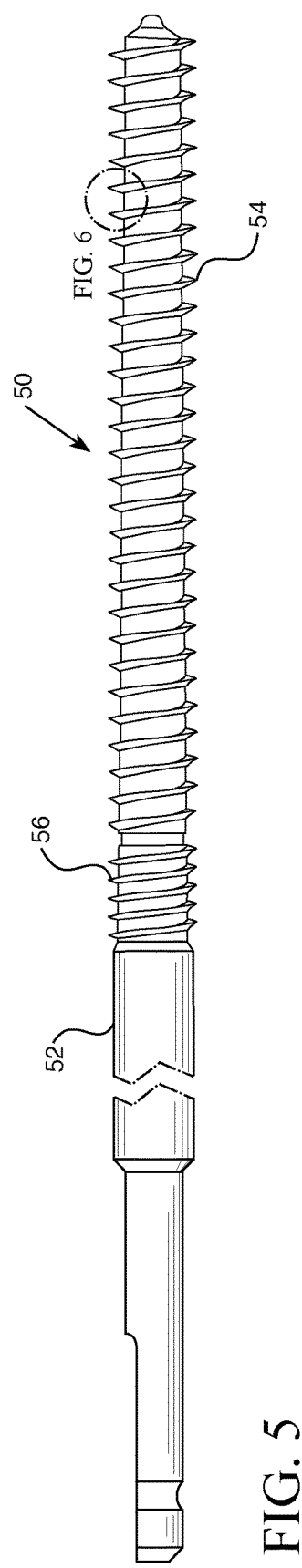
FIG. 5 is a side elevational view of the second embodiment of the present half pin as shown in FIGS. 2 and 4.
Figure 5A:
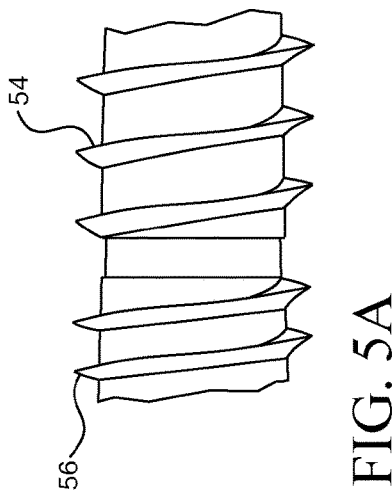
FIG. 5a is a partial close-up view of the area of FIG. 5 where the thread pitch changes.

Those familiar with already existing bone screws and compression screws know very well that when an increasing diameter screw is used to penetrate bone, the cost of any mistake can be great. When a bone screw is placed perfectly the first time, there is of course no problem. However, when a surgeon, particularly but not limited to an intern or a resident, puts a bone screw in—initially at the incorrect angle or in the incorrect place—the difficulties attendant in removing such a screw are complicated if the taper of the implant has increased too much along its length. Overly increasingly—tapered screws will create too much compression and too big of a hole in the bone, and if a first screw has "to be backed out" then a larger screw will need to be substituted upon the next insertion attempt. One of the benefits of the present half pin inheres in the tip end of the threads' having uniform outer (major) diameter threads whereas the inner (minor) diameter of the threads only slowly increases from the tip toward the head of the pin—and only partway through the span of threads (see FIGS. 5 and 5a). At the point in the threads where the threads become tighter in pitch, a chamfer and a stepwise reduction in inner diameter also create a practical fail safe for the surgeon. In the event that the half pin is inserted up to the tighter pitch chamfer but needs to be removed at that point, the gradual increase of the inner diameter up to that point will not appreciably compromise the aperture in the bone into which the half-pint has been disposed, and the surgeon can try again. At the same time the gradual increase of the inner diameter does provide a beneficial compressive force as the half-pin is inserted through the bone or bones, to enhance the grip of the threads in the adjacent bone.

The segment of tighter pitch threads (see FIGS. 5 and 5a) is particularly designed to interface with the cortical bone, that is, the edge of the bone or one of the bones to be secured. For this reason, the present half pins have threaded lengths that are available commercially in successive 5 mm increments, so that the surgeon can choose a thread length that is approximately the same length as the side to side length of the bone or bones span to be secured (or tissue to be bridged in the case of a non-bone fixation). The tighter pitch of the threads provides a compressor function and after the entire threaded portion of the half pin is in place, the compression screw function of the tighter pitch threads cinches and pressurizes the bone or bones (or tissue) into their desired position. This cinching or pressuring is also therapeutic to the bone—sometimes this pressure is referred to as "physical therapy" for the bone—because when bones are subjected to the internal and external pressures caused by the threads of the half pin, bone growth is directly stimulated by such pressures, and this bone growth is entirely consistent and advantageous to the repair being made with the fixator system overall.

Apart from the threaded region of the half pin and the adjacent tapered region, and the connector at the head end, it is important that the full shaft maintain the same diameter throughout to assure minimization of shock stress to the shaft such as might cause shaft failure. With a full and consistent shaft thickness throughout the length of the half pin, again, not counting the AO or other connector or the threaded region or its associated adjacent taper, the half-pin provides the maximum load-bearing shaft between the bone and the cooperating external fixator hardware.

The present inventors have already confirmed that the hydroxyapatite coated wire or half pin (hydroxylapatite and hydroxyapatite are synonyms for the purpose of this specification) are able to perform an antimicrobial or antibacterial effect, as discussed above. The inventors have already noted in clinical trials that a hydroxyapatite coated half pin will provide a clean surgical site during recovery whereas a conventional uncoated half pin will often be associated with infection in the surrounding skin, even if the two different pin types are only inches apart and thus subjected to the same microbial assaults. In designing the hydroxylapatite coating, several engineering features have been determined to be important, as discussed above and more particularly here. In addition to the thickness of the hydroxyapatite coating, the coating must also be porous within specified tolerances. In general, the porosity is 5% or less based on the dimensions or mass of the coating, and the average pore size will in generally be between 5 and 10 micrometers, and more preferably 6.3 micrometers plus or minus 6 micrometers. In theory, although applicants do not wish to be bound by the theory, the porosity enhances the ability of the adjacent skin and surrounding tissue of the patient to adhere partially—and only partially—to the half pin and to form a desirably crusty and dry protective—almost callous like—surface around the half pin. Ironically, for antimicrobial effect, one ultimately does want the skin and tissue to crust and dry around the half pin, because it is a moist environment which turns out to foment the worst half-pin-associated local infections and the drier skin tends not to get infected. The above-described porosities and the disclosed hydroxyapatite coating thickness foment the best of both situation of, as mentioned heretofore, a seal for antimicrobial purposes but not so much tissue adherence to create discomfort upon ultimate removal of the half pin (or wire) from the patient.

Typical hydroxyapatite coatings can be provided by, for example, Orchid Orthopedic Solutions, but hydroxyapatite in itself and hydroxyapatite coating are generally already well known. Typical hydroxyapatite coatings of the present invention have a hydroxyapatite content of greater than 98% with a percentage crystallinity of at least 68%, and the calcium to phosphorus ratio is ideally 1.67. It should also be noted that the hydroxyapatite coatings of the present invention have a tensile strength of on the order of 9429 plus or minus 1595 pounds per square inch. It is believed that the porosity of 5% or less is important both in creating adequate porosity for partial attachment and drying of the adjacent tissue, without loss of integrity in the hydroxyapatite coating due to the presence of excess porosity.

Generally speaking, there is nothing except cost that would prevent the coating of the entire half pin with hydroxyapatite. As a practical matter, the hydroxyapatite coating need only to extend distal to the threads for so far as the half pin shaft exist the skin of the patient. For large or obese patients, it is possible that more than 50 mm of the shaft distal of the threads would need to be covered, but the above-described coating dimensions are suitable for most patients.

When wires are used in place of half pins, wires are typically not threaded and the hydroxyapatite coating extends at least from the bone to the outside of the patient's body. Both wires and half pins need to be used in cooperation with a corresponding drill, that provides the aperture or channel in the bone or bones into which the wire or half pin will be inserted. In other words, the present wires and half pins are not self-cutting. The use of a cooperating drill and appropriately sized drill bit facilitates positioning of the aperture for the half pin or a wire near the joint or metaphyseal or diaphyseal bone into which the wire or half pin will be inserted.

The present wires and half pins may be used in association with any or all of external circular fixators, hexapod fixators or monolateral or unilateral rail fixators. The present half pins may be manufactured with standard AO connector head ends or may bear any sort of connection device. In some cases when the AO device passes through an aperture in a securement means on a fixator, it is customary to cut or truncate the AO connector and cap the cut end with a rubber or other polymer cap. For a 6 mm half pin, the cap would have a 6 mm aperture to match the cut end.

As is already typical in the external fixator arts, the surgeon can insert the present wires or half pins with hand tools such as screwdrivers or using powered insertion tools. Typically the half pins are available in 5 mm or 6 mm gauges, with the 5 mm half pins having any of 5 mm, 4 mm or 3 mm outer diameter of threads. For the 6 mm family of half pins, the outer diameter of threads are typically any of 6 mm, 4.5 mm or 3 mm. Not only are the thread lengths available in a variety of 5 mm increments from 10 mm to 60-90 mm increments, but the overall pin or half pin lengths are available in a wide range of sizes to suit any patient or application including pediatric applications. The 60 to 90 mm thread lengths are typical thread lengths for the repair of the tibia or femur. Interestingly, thread diameter of the half pins should be no larger than ⅓ the diameter of the bone in which the half-pin is to be implanted, for reasons of biological and physical reality as to concomitant stress.

As described above and highlighted here, if there is any one overriding benefit in the present structural makeup of the half pin of FIG. 2, it is in the location of the compression threads, that is, the proximal position of the relatively tighter pitch threads, and the ability of those threads to exert "good cortical purchase" in the cortical bone where they will compress the bone, if the correct thread length to match the bone or bones span has been selected.

Referring now to the drawings, FIGS. 1-3 show three different embodiments 10, 20 and 30 of the present half pin, having different threads and configurations. FIG. 2 shows an embodiment of the invention which contains certain interesting features, including a rounded "nipple" tip 22 and particularly engineered threads 24. Whereas the threads 14 and 34 of FIGS. 1 and 3, respectively, are constant pitch threads with constant inner and outer diameters, the threads 24 of FIG. 2 have been particularly engineered and are shown further in FIGS. 4, 5 and 5a.

FIG. 4 shows the half pin 40 in sectional view, with major shaft 42 and a threaded segment made up of tip threads 44 and tighter threads 46, at either side of a reduced diameter space with chamfer (not shown). The detail of the thread transition is more clearly shown in FIG. 5A. The inner, minor diameter increases slightly, in the area of the larger pitch threads nearest the half pin tip, progressing from the half pin tip to the transition area where the thread pitch of threads 56 becomes tighter. At the transition between thread pitches, there is a decrease in minor diameter together with a chamfer (not shown), which is there as a reality of machining the tighter pitch threads and needing room to get the necessary cutting tool in place to manufacture the tighter pitch threads. The decrease in minor diameter also provides a fail-safe for the surgeon, to prevent too much compression due to inner (minor) diameter increase in the event that the half pin needs to be removed and repositioned.

Figure 6:
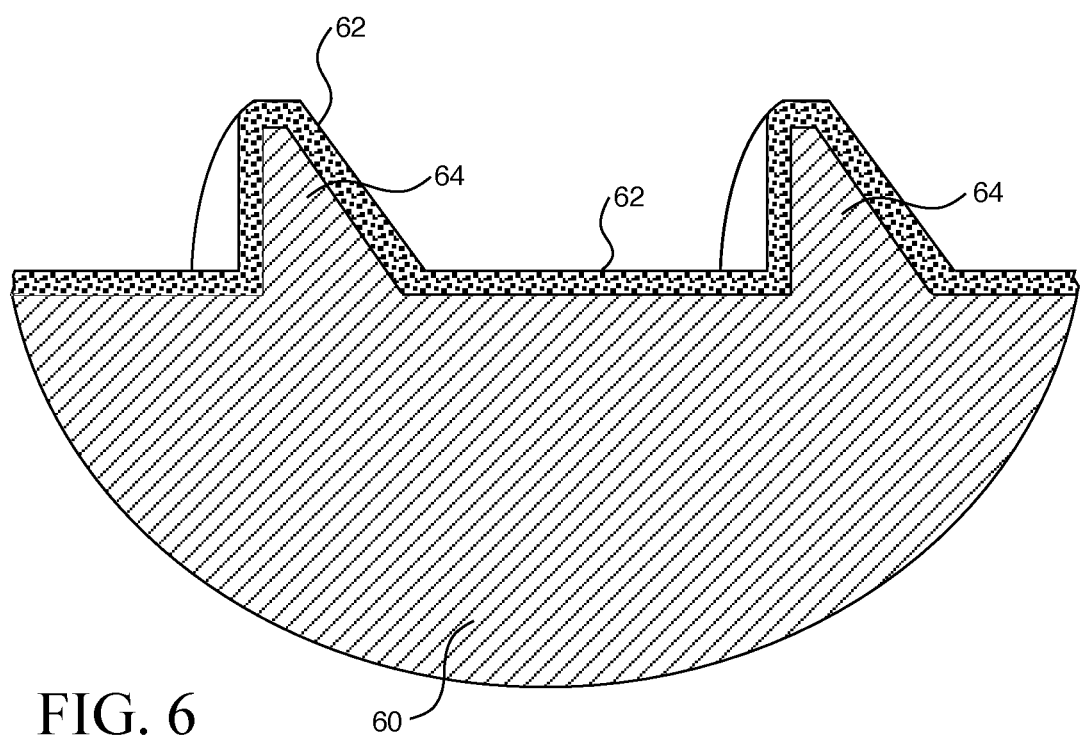
FIG. 6 is a cross section of the distal thread area of FIG. 5.

FIG. 6 shows, in section, the half pin 60 with hydroxyapatite coating 62 on threads 64. The hydroxyapatite coating has thickness and porosity characteristics as discussed above, and as shown is generally continuous even over the outside surfaces of the half pin threads.

Figure 7:
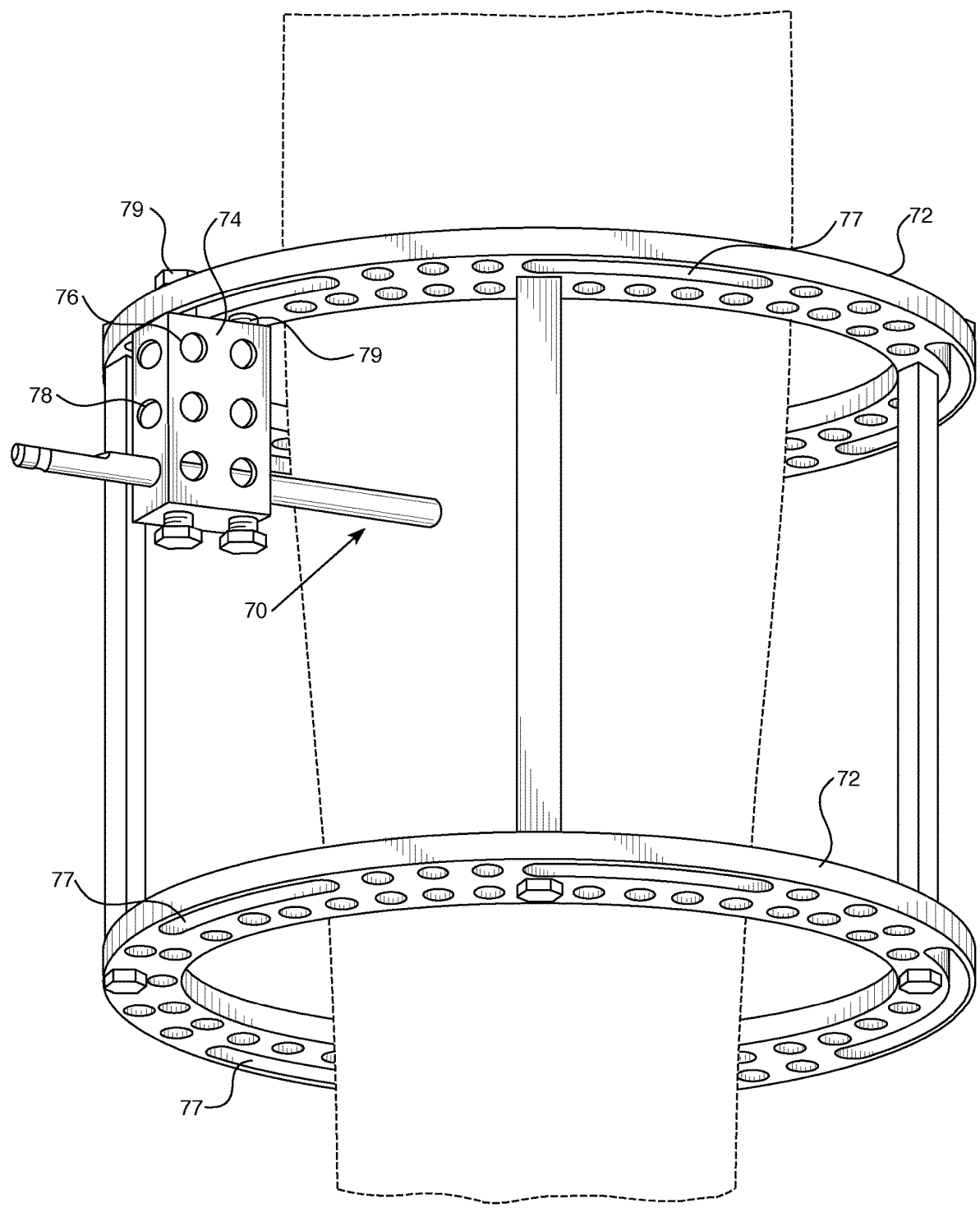
FIG. 7 is a perspective view of a pair of external fixator rings affixed to a patient limb (shown in dotted lines) via a pin cube according to the present invention.

Referring now to FIG. 7, a half pin 70 is affixed to external fixator rings 72 by a pin cube 74, which is a hollow titanium cube having pin cube holes 76 and channel holes 78 therein. Top and bottom pin cube holes are fitted with pin bolts 79 as illustrated. The cube provides multiple orientation possibilities for the present half pins, which otherwise would be affixed to the rings 72 with far fewer positional choices. In particular, when the rings have both holes and slots 77 as illustrated, a wide variety of angles of attachment of the pin bolts 79 to the rings is possible, because the pin bolts 79 can be rotated within the ring slots 77 when needed to provide the desired half pin angle. For strength and to avoid failure, the pin cube 74 is always constructed of surgical grade titanium. In FIG. 7, the dotted lines represent a patient limb. Having two pin bolts 79 affixed to two points on the fixator ring 72 assures rotational stability not only for the pin cube 74, but for the associated half pin 72 as well.

As an added benefit, the pin cube can be suspended on occasion from a single hole on the inner circumference of the ring, when you need to reduce the lever arm of the half pin. Even the little bit of shortening of the shaft length that you get, by in effect hanging the pin cube from a single hole adjacent the inner circumference of the ring, gives you a Torque=Force×Distance benefit with respect to reducing stress on the half pin between the bone and the external fixator. In other words, if you need "to cheat the length" of a half pin in any given surgical installation, it is easily possible to move the pin cube from spanning two holes on the fixator ring, or one hole and one slot, to give positioning flexibility to the pin cube, while simply adhering the pin cube via one pin bolt to one hole in the fixator ring. In reviewing the affixing alternatives of the pin cube to the ring, it becomes apparent that some judgment of the surgeon is needed—how long are the pin distances, what are the forces involved, and how much of the stability afforded by the two points of attachment on the ring can be sacrificed in favor of the different but equally important reduction of stress by reducing the length of the lever arm of the half pin? A useful features of the present hardware is that all the above options are preserved, for use at the discretion of the surgeon.

Figure 8:
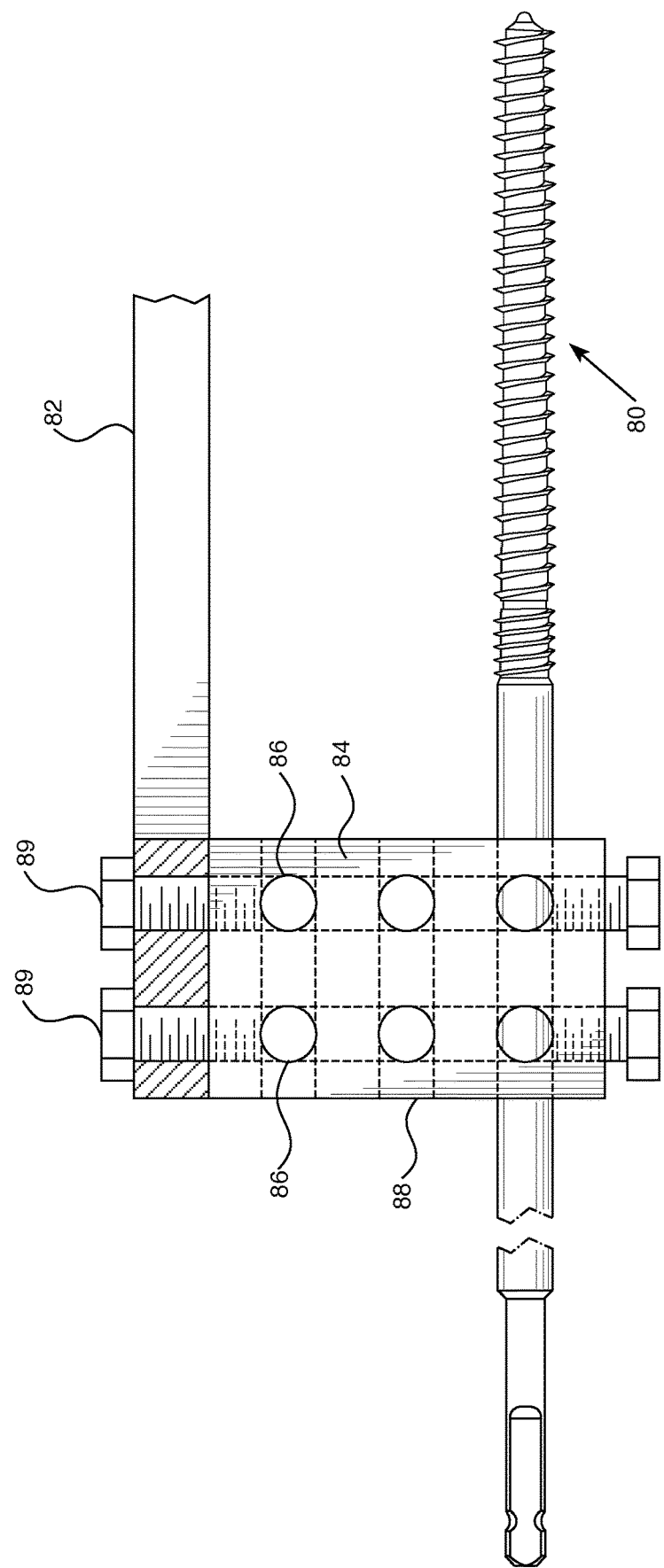
FIG. 8 is a side elevational view of the pin cube of FIG. 7, showing in greater detail the securing of the half pin with end bolts.
Figure 9:
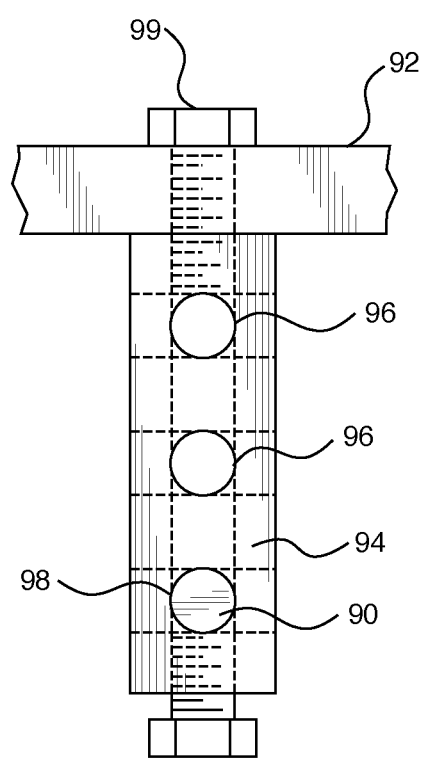
FIG. 9 is an end view of the pin cube according to FIG. 8.

Referring now to FIG. 8, the pin cube 84, with its pin cube holes 86 and pin channels 88 to secure a half pin 80 to a ring 82, are all the same as the structures shown in FIG. 7—as are the analogous structures of FIG. 9.

Figure 10:
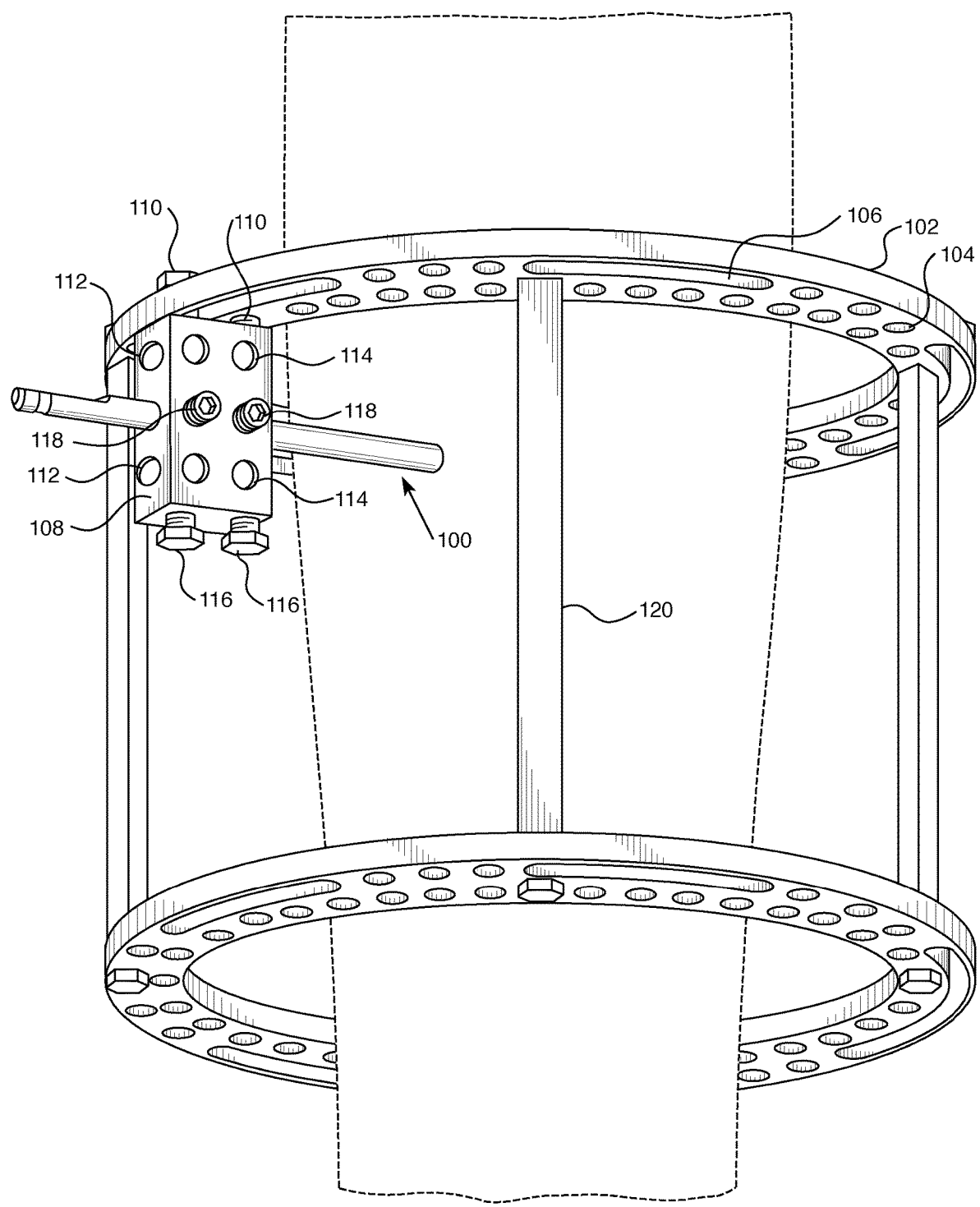
FIG. 10 is a perspective view of a pair of external fixator rings affixed to a patient limb (shown in dotted lines) via the same pin cube as shown in FIG. 7, except that the half pin is secured through a center channel of said pin cube with set screws.

Referring now to FIG. 10, the half pin 100 is secured to the ring 102 by pin cube 108, in this view through the middle of the three pin block channels 112 rather than at the top or the bottom of the pin cube 108. The pin cube is affixed at the top via pin cube bolts 110 to the ring 102. Set screws 118 hold the half pin 100 to the center channel 112 of the pin cube 108. Set bolts 116 are not in use as shown in FIG. 10, but could be used to hold a half pin in position in the bottom channel 112 or, were the pin cube to be reversed 180 degrees, the set bolts 116 would become the pin cube bolts 110 and could be used to affix the pin cube 108 to the ring 102. The shaft 120 is representative of any number of shafts that can be used to connect external fixator rings, in either static or dynamic fashion. Pin cube holes 114 are there to provide additional half pin positions adjacent the bottom or top channels and set screws such as set screws 118 can be used in these holes as needed.

What is claimed is:

1. A half pin for use in an external fixator, the half pin comprising:
    a head end;
    a leading tip at a distal end; and
    both an unthreaded shaft and a threaded shaft in between said head end and said leading tip,
    wherein said unthreaded shaft is at least as long as said threaded shaft, and
    wherein said threaded shaft has threads of a first pitch and has threads of a second pitch, said threads of said first pitch and said threads of said second pitch being disposed distally to said unthreaded shaft, said threads of said second pitch being more distally disposed to said unthreaded shaft than said threads of said first pitch, said second pitch being larger than said first pitch, said threads of said first pitch having a uniform first major diameter and a uniform first minor diameter, said threads of said second pitch having a uniform second major diameter, said threads of said second pitch having a first end proximal to said leading tip, wherein said leading tip is unthreaded and said threads of said second pitch comprise the threads closest to said unthreaded leading tip, said threads of said second pitch having a second end proximal to said threads of said first pitch, said threads of said second pitch having a second minor diameter gradually increasing from said first end to said second end.

2. The half pin according to claim 1, wherein said threaded shaft includes an axially-extending portion separating said threads of said first pitch from said threads of said second pitch, and said axially-extending portion has an outer diameter being smaller than said first minor diameter and smaller than said second minor diameter at said second end.

3. The half pin according to claim 2, wherein said second pitch is about 1.7 mm and said first pitch is about 1.2 mm.

4. The half pin according to claim 1, wherein at least a portion of said threaded shaft and at least a substantial portion of said unthreaded shaft are coated with a 40-70 micron plasma-spray-deposited hydroxyapatite coating.

5. The half pin according to claim 4, wherein said hydroxyapatite coating has between 1-5% porosity.

6. The half pin according to claim 5, wherein said hydroxyapatite coating has a pore size diameter of 10 micrometers or less.

7. The half pin according to claim 6, wherein each of said head end, said leading tip, said unthreaded shaft, and said threaded shaft comprise a surgical stainless steel.

8. The half pin according to claim 4, wherein said threaded shaft includes an axially-extending portion separating said threads of said first pitch from said threads of said second pitch, and said axially-extending portion has an outer diameter being smaller than said first minor diameter and smaller than said second minor diameter at said second end.

* * * * *